United States Patent
Huiku

(10) Patent No.: US 8,246,546 B2
(45) Date of Patent: Aug. 21, 2012

(54) METHOD, ARRANGEMENT AND APPARATUS FOR MONITORING FLUID BALANCE STATUS OF A SUBJECT

(75) Inventor: Matti Huiku, Espoo (FI)

(73) Assignee: General Electric Company, Schenectady, NY (US)

( * ) Notice: Subject to any disclaimer, the term of this patent is extended or adjusted under 35 U.S.C. 154(b) by 903 days.

(21) Appl. No.: 12/241,480

(22) Filed: Sep. 30, 2008

(65) Prior Publication Data

US 2010/0081942 A1    Apr. 1, 2010

(51) Int. Cl.
*A61B 5/02* (2006.01)
*A61B 5/145* (2006.01)

(52) U.S. Cl. ........................................ 600/483; 600/309
(58) Field of Classification Search ................. None
See application file for complete search history.

(56) References Cited

U.S. PATENT DOCUMENTS

| | | | |
|---|---|---|---|
| 5,709,670 A * | 1/1998 | Vancaillie et al. | 604/246 |
| 6,400,972 B1 | 6/2002 | Fine | |
| 6,587,704 B1 | 7/2003 | Fine et al. | |
| 6,711,424 B1 | 3/2004 | Fine et al. | |
| 6,974,418 B1 * | 12/2005 | Hutchinson et al. | 600/481 |
| 2009/0024011 A1 | 1/2009 | Huiku | |
| 2009/0326342 A1 | 12/2009 | Huiku | |
| 2010/0099964 A1 | 4/2010 | O'Reilly et al. | |

OTHER PUBLICATIONS

Aoyagi et al., "Blood Volume Measurement at the Bedside Using ICG Pulse Spectrophometry", American Society of Anesthesiologists, Inc., vol. 89(6), Dec. 1998, pp. 1322-1328.

* cited by examiner

*Primary Examiner* — Shanon A Foley
(74) *Attorney, Agent, or Firm* — Andrus, Sceales, Starke & Sawall, LLP

(57) ABSTRACT

A method and apparatus for monitoring fluid balance status of a subject are disclosed. A hemoglobin measure indicative of hemoglobin concentration in the blood of a subject and at least one physiological parameter responsive to blood volume changes in the subject are determined and concurrent behavior of the hemoglobin measure and the at least one physiological parameter is indicated to a user, thereby to give an indication of fluid balance status of the subject. The cause and/or reliability of the fluid balance status may also be indicated.

20 Claims, 4 Drawing Sheets

METHOD, ARRANGEMENT AND APPARATUS FOR MONITORING FLUID BALANCE STATUS OF A SUBJECT

BACKGROUND OF THE INVENTION

This disclosure relates generally to monitoring of fluid balance status of a subject, and to a mechanism indicative of the fluid balance status of the subject and the form of fluid therapy needed for the subject.

A vast majority of hospitalized patients and all patients undergoing a surgery have an intra-venous (IV) catheter placed to deliver different types of medications for inducing and maintaining anesthesia and/or for infusing fluid volume and blood products, for example. Since the health and safety of the patient is often at stake, an IV infusion system must perform at the highest possible effectiveness, and the patient shall be monitored for early detection of a possible crisis situation. However, current practices in IV therapy seldom include effective crisis management with adequate monitoring and early detection of the effects of the infusions in the patient.

Effective fluid management is based on maintenance of correct fluid balance in human body. In a simple physiological model the water content of the human body is divided into three main fluid compartments: blood, interstitial body fluid (between cells), and intracellular fluid. Usually the intracellular fluid compartment is rather stable, but because of the rapid interchange of fluids that may take place between blood plasma and the interstitial compartment in sepsis and inflammatory states, for example, fluid distribution may change continuously in acute care patients. Further, in operating theatres and during post-operative care, blood and fluid loss may be considerable, which may lead, in an extreme case, to an acute need of blood transfusion and infusion of massive amounts of fluids. Excessive fluid (hypervolemia) may lead to hypertension, heart failure, pulmonary edema or electrolytic imbalance, while too little fluid (hypovolemia) may cause hypotension, hemodynamic collapse, blood centralization, or electrolyte imbalance.

Fluid management may involve infusion of crystalloid solutions, such as physiological saline, colloids or glucose solutions, depending on which compartment of body fluid is most disturbed. Crystalloids fill both the blood plasma and the interstitial compartments, while colloids fill only the plasma compartment. Glucose (small molecule) solutions are used to correct the fluid content of the whole body. In acute care, nutrition and tight glucose control are also beneficial to the patient, and there is also clinical evidence that an effective fluid management can improve patient outcome and reduce hospital costs in acute care.

The clinical signs that are associated with hypo- and hypervolemia, i.e., physiological volemia parameters, are often confounded by various other physiological mechanisms, and are thus unspecific. Still the assessment of volemia parameters requires invasive catheterization, which cannot be justified, if the catheter is not needed for other clinical assessments or IV drug delivery. Further, the control of fluids is currently based on very variable clinical rule sets, since both quantitative measurement of the fluid compartment volumes and the monitoring of the effects of hypo- and hyperfluidity is cumbersome.

Monitoring of blood volume requires that the concentration of a blood substance is measured. Traditionally, the blood volume of a subject has been estimated through an in-vitro analysis of one or more blood samples taken from the subject, by determining the hemoglobin dilution in the samples, i.e., hemoglobin is used as the blood substance whose concentration change is determined before and after diluting the blood with a known amount of fluid.

In order to obviate the continuous blood sampling, it has been suggested to use pulse oximeter technology for measuring the concentration of a tracer substance in blood In a method like this, a known amount of a tracer substance, such as indocyanine green dye, is injected into the subject and the concentration of the substance in the blood is tracked using pulse oximeter technology. The determination of the tracer substance concentration requires that a hemoglobin concentration is determined a priori, as it is used as a reference concentration, to which the measured optical signals are compared. At least one blood sample is thus needed. Based on the tracer concentration, blood volume may be determined, but the measurement is at most semi-continuous, because the dye injection can be repeated only after certain time interval, depending on how fast the dye is eliminated from blood.

However, the hemoglobin concentration measurement or the physiological volemia parameters alone are not specific enough to determine the IV therapy form needed in each individual case. For instance, when the patient looses blood by leaking into the cavities of the abdomen, the hemoglobin concentration does not necessarily change, and hypovolemia can be detected only after the blood pressure compensation mechanisms fail. In this case, the physiological volemia parameters may react to the centralization of blood circulation and may thus reveal the blood leak early enough to start a correcting therapy. The right therapy form is in this case infusion of colloids or crystalloids and, if needed, blood products, to maintain tissue oxygenation and cardiac function. On the other hand, when a part of blood plasma volume runs away to the interstitial fluid compartment, the hemoglobin concentration increases and usually reveals the adverse event and the colloid therapy can be started. The most common fluid administration failure is infusion of too much fluids, which may be caused by human error simply by forgetting, in an emergency situation, to stop rapid fluid expansion. In this case the hemoglobin is diluted and the volemia parameters react simultaneously to the overload of fluid in a patient. Cardiac failure or pulmonary edema can be avoided by stopping infusions and/or medicating the patient as needed.

The drawback of current technology is that it does not allow a comprehensive, easy and quantitative assessment of the fluid balance in a patient. Furthermore, current mechanisms for assessing the fluid balance of a subject are not specific enough for identifying the various reasons behind sudden blood volume changes and thus cannot unambiguously indicate towards the correct form of fluid therapy.

BRIEF DESCRIPTION OF THE INVENTION

The above-mentioned problems are addressed herein which will be comprehended from the following specification.

In an embodiment, a method for monitoring fluid balance status of a subject comprises determining a hemoglobin measure indicative of hemoglobin concentration in blood of a subject, wherein the determining includes determining successive values of of the hemoglobin measure. The method further comprises defining at least one physiological parameter responsive to blood volume changes in the subject, wherein the defining includes defining successive values for the at least one physiological parameter, and indicating concurrent behavior of the hemoglobin measure and the at least one physiological parameter, thereby to give an indication of fluid balance status of the subject.

In another embodiment, an arrangement for monitoring fluid balance status of a subject comprises a hemoglobin measurement unit configured to determine a sequence of a hemoglobin measure indicative of hemoglobin concentration in blood of a subject and a physiological parameter unit configured to define a sequence of at least one physiological parameter responsive to blood volume changes in the subject. The arrangement further comprises an indicator unit configured to receive the sequence of the hemoglobin measure and the sequence of the at least one physiological parameter, and to indicate concurrent behavior of the hemoglobin measure and the at least one physiological parameter, thereby to give an indication of fluid balance status of the subject.

In a still further embodiment, an apparatus for monitoring fluid balance status of a subject comprises a data interface unit configured to receive successive values of a hemoglobin measure indicative of hemoglobin concentration in blood of the subject and successive values of at least one physiological parameter responsive to blood volume changes in the subject and a display control unit configured to generate, based on the successive values of the hemoglobin measure and the at least one physiological parameter, display data indicative of concurrent behavior of the hemoglobin measure and the at least one physiological parameter, thereby to give an indication of fluid balance status of the subject.

Various other features, objects, and advantages of the invention will be made apparent to those skilled in the art from the following detailed description and accompanying drawings.

DETAILED DESCRIPTION OF THE INVENTION

Figure 1:
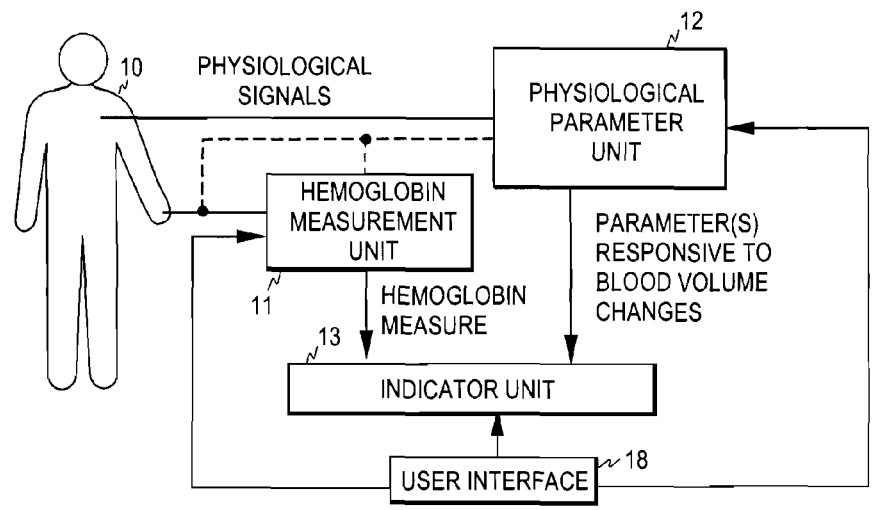
FIG. 1 illustrates one embodiment of a system for monitoring the fluid balance of a subject.

FIG. 1 illustrates an embodiment of a system for monitoring fluid balance of a subject 10. The system comprises a hemoglobin measurement unit 11 for measuring a hemoglobin measure indicative of the hemoglobin concentration of the subject. The determination of the hemoglobin measure may be carried out non-invasively and continuously, thereby to obtain hemoglobin concentration trend. Although the hemoglobin measure may indicate the actual hemoglobin concentration (g/dl or equivalent units) or the volume fraction of the red cells containing hemoglobin, i.e., hematocrit, that directly indicates the hemoglobin concentration in the whole blood, it may also be a measure indicative of the relative value of hemoglobin concentration or changes therein.

The system further comprises a physiological parameter unit 12 for measuring successive values for at least one physiological parameter responsive to the blood volume changes in the subject. Since the parameter(s) determined in unit 12 are responsive to the blood volume changes in the subject, the said parameter(s) is/are also termed blood volume parameter(s) in this context. As discussed below, the blood volume parameter(s) may be indicative of cardiac preload, i.e. of the blood volume returning to the heart of the subject, for example. Furthermore, each final blood volume parameter output from unit 12 may be an enhanced parameter derived from several different blood volume parameters or from successive values of one blood volume parameter.

The system further comprises an indicator unit 13 for indicating the prevailing relationship between the hemoglobin measure and the blood volume parameter(s) defined in the physiological parameter unit. The prevailing relationship may include not only the current values of both the hemoglobin measure and the blood volume parameters, but also the current trends thereof. Since a determined blood volume parameter is responsive to the blood volume changes in the subject, it is also indicative of changes in the volemia status of the subject, which may require an immediate fluid management operation to improve the fluid balance of the subject. However, as the said parameter(s) are not specific to such changes only, but may react to various events, such as changes in the pose of the subject, the hemoglobin measure may be used to verify if a fluid management operation is really needed. The prevailing relationship between the hemoglobin measure and the blood volume parameter(s), i.e., concurrent behavior of the hemoglobin measure and the blood volume parameter(s), is indicative of the said need.

The operation of the system may be controlled through an appropriate user interface 18, through which all units 11, 12, and 13 may be controlled by the user.

In a simple embodiment, the indicator unit shows the hemoglobin trend and the trend(s) of the blood volume parameter(s) defined. Based on the simultaneous temporal behaviour of the hemoglobin concentration and the parameter(s), the user is informed of the fluid balance status of the subject. The above-mentioned enhanced parameter(s) may also be calculated in the indicator unit. In more sophisticated embodiments, the indicator unit 13 may calculate quantitative blood volume estimates, give an assessment of the volemia status of the patient, and/or suggest the correct fluid therapy form. The indicator unit may further calculate a quality/reliability index that indicates the reliability/quality of the assessment of the fluid balance status.

Below, the different units of FIG. 1 are discussed in more detail starting from the hemoglobin measurement unit 11.

The hemoglobin measurement unit 11 may comprise any unit capable of measuring the hemoglobin measure substantially continuously, thereby to obtain a sequence of hemoglobin measure values. However, it is beneficial if the hemoglobin measure may be determined non-invasively, since non-invasive hemoglobin measurements have clear advantages, which include the elimination of both painful blood sampling and the risk of infection. Non-invasive optical hemoglobin measurements in-vivo are typically based on artificially induced changes in the blood flow of the patient. The measurement unit may comprise, for example, a measurement device based on a so-called occlusion-release (OR) measuring technique. A typical OR based measurement device utilizes a ring-shaped cuff applied to the patient's finger. The device is further provided with a pressurizing arrangement to produce a state of temporary blood flow cessation in the finger by applying an over-systolic pressure and a state of transitional blood flow by releasing the over-systolic pressure. Measurement sessions are carried out during various states of blood flow and the blood absorption characteristics during the said states are analyzed to determine the concentration of a blood constituent, such as hemoglobin.

The hemoglobin measurement unit may also be based on a cerebral pulse oximeter that employs measurement electrodes attached to the forehead of the patient.

Figure 2:
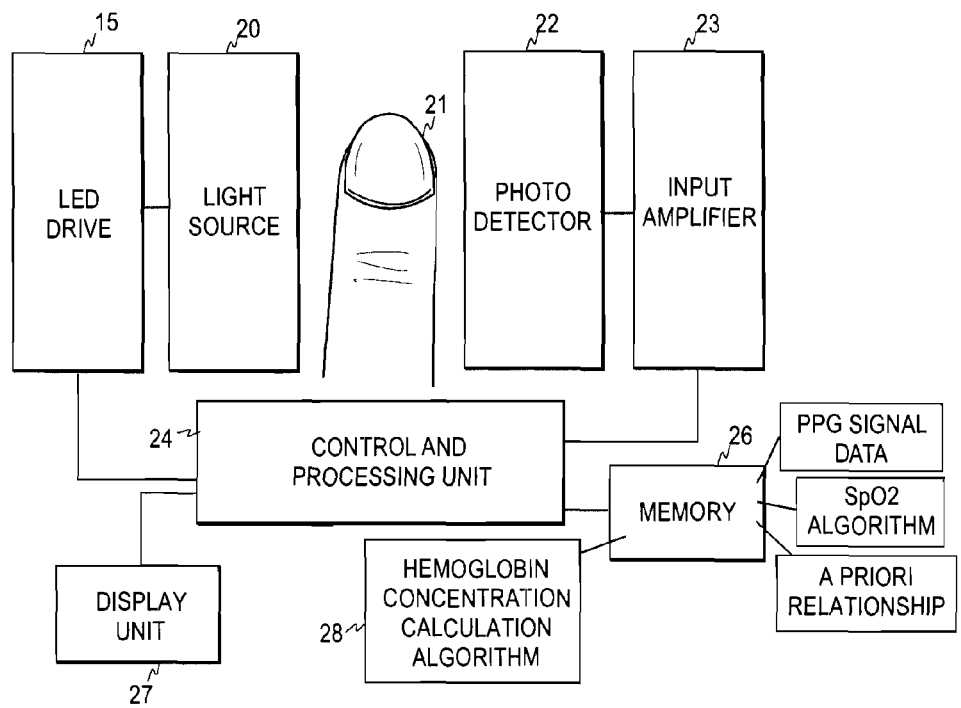
FIG. 2 is a block diagram illustrating one embodiment of a pulse oximeter based unit for determining a sequence of hemoglobin measures indicative of the hemoglobin concentration of a subject.

However, in one embodiment the hemoglobin measurement unit is based on a conventional finger/ear pulse oximeter upgraded with a mechanism for determining the concentration of hemoglobin in the blood of a subject. FIG. 2 illustrates this embodiment of the hemoglobin measurement unit 11. The hemoglobin measurement unit is based on a pulse oximeter, which normally comprises a computerized measuring unit and a probe attached to the patient, typically to a finger or ear lobe. The probe includes a light source for sending an optical signal through the tissue and a photo detector for receiving the signal transmitted through or reflected from the tissue. On the basis of the transmitted and received signals, light absorption by the tissue may be determined. During each cardiac cycle, light absorption by the tissue varies cyclically. During the diastolic phase, During the diastolic phase, absorption is caused by venous blood, non-pulsating arterial blood, cells and fluids in tissue, bone, and pigments, whereas during the systolic phase there is an increase in absorption, which is caused by the inflow of arterial blood into the tissue part on which the sensor is attached. Pulse oximeters focus the measurement on this pulsating arterial blood portion by determining the difference between the peak absorption during the systolic phase and the background absorption during the diastolic phase. Pulse oximetry is thus based on the assumption that the pulsatile component of the absorption is due to arterial blood only.

In order to distinguish between two species of hemoglobin, oxyhemoglobin ($HbO_2$) and deoxyhemoglobin (RHb), a traditional pulse oximeter must measure absorption at two different wavelengths, i.e. the probe of a traditional pulse oximeter includes two different light emitting diodes (LEDs) or lasers. The wavelength values widely used are 660 nm (red) and 940 nm (infrared), since the said two species of hemoglobin have substantially different absorption at these wavelengths. Each LED is illuminated in turn at a frequency which is typically several hundred Hz.

With reference to FIG. 2, light transmitted from a light source 20 including a plurality of LEDs or lasers passes into patient tissue, such as a finger 21. As discussed below, the number of wavelengths used in the pulse oximeter may vary. However, at least two LEDs (wavelengths) are required for oxygen saturation measurement.

The light propagated through or reflected from the tissue is received by a photodetector 22, which converts the optical signal received at each wavelength into an electrical signal pulse train and feeds it to an input amplifier 23. The amplified signal is then supplied to a control and processing unit 24, which converts the signals into digitized format for each wavelength channel. The digitized signal data is then utilized by an $SpO_2$ algorithm. The control and processing unit executes the algorithm and drives a display 27 to present the results on the screen of the display. The $SpO_2$ algorithm may be stored in a memory 26 of the control and processing unit.

The control and processing unit further controls a source drive 15 to alternately activate the LEDs. As mentioned above, each LED is typically illuminated several hundred times per second. The digitized photoplethysmographic (PPG) signal data at each wavelength may also be stored in the said memory before being supplied to the $SpO_2$ algorithm.

With each LED is illuminated at such a high rate as compared to the pulse rate of the patient, the control and processing unit obtains a high number of samples at each wavelength for each cardiac cycle of the patient. The value of these samples varies according to the cardiac cycle of the patient.

In order for variations in extrinsic factors, such as the brightness of the LEDs, sensitivity of the detector, or thickness of the finger, to have no effect on the measurement, each signal received is normalized by extracting the AC component oscillating at the cardiac rhythm of the patient, and then dividing the AC component by the DC component of the light transmission or reflection. The signal thus obtained is independent of the above-mentioned extrinsic factors.

A conventional pulse oximeter of the above type is upgraded with a mechanism for determining a hemoglobin measure indicative of the hemoglobin concentration of a subject. For this purpose, a calculation algorithm 28 may be stored in the memory of the pulse oximeter. The control unit executes the algorithm which may utilize the same digitized signal data as the $SpO_2$ algorithm, or the results derived in the $SpO_2$ algorithm. Compared to a standard two-wavelength pulse oximeter, the pulse oximeter of the hemoglobin measurement unit 11 is further provided with at least one extra wavelength for the hemoglobin measurement.

Figure 3:
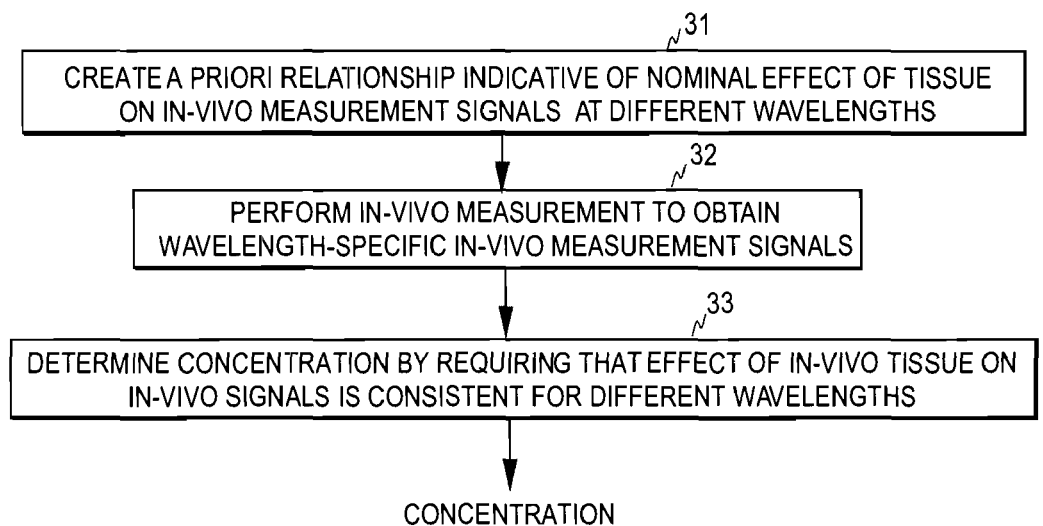
FIG. 3 is a flow diagram illustrating one embodiment for determining the hemoglobin measure.

FIG. 3 illustrates one embodiment for determining the hemoglobin concentration in the hemoglobin measurement unit. An a priori relationship is first formed, which is indicative of the (nominal) effect of the tissue on in-vivo measurement signals at the wavelengths of the apparatus (step 31). In-vivo measurement signals here refer to signals obtained from a living tissue. The nominal condition represents the normal concentrations of a blood substance for a typical population of subjects. The in-vivo measurement signals are then measured from in-vivo tissue at different wavelengths (step 32). The concentration of the blood substance (i.e., hemoglobin in this case) may be determined based on the a priori relationship by requiring that the effect of the in-vivo tissue on the in-vivo signals remains consistent for all wavelengths at which the in-vivo measurement is performed (step 33). Consistency may be found based on the a priori relationship.

Although the a priori relationship created may be constructed empirically, it may also be based on a tissue model obtained by adding interactions to a known model, such as the Lambert-Beer model. The tissue model so obtained typically includes a number of parameters, one of the parameters being a tissue parameter which is indicative of the concentration of the blood substance. The a priori relationship may be created with nominal tissue parameter value and the relationship may describe the effect of the tissue on a predetermined parameter derivable from the in-vivo signals, wherein the predetermined parameter is such that the effect, which is wavelength-dependent, may be seen in it.

Consistency is then detected based on the predetermined parameter and the a priori relationship. However, the criterion indicating the occurrence of consistency depends on the predetermined parameter utilized. In one embodiment, a theoretical value for the predetermined parameter is determined. This theoretical value may be calculated using an ideal tissue, such as only the pulsating arterial blood in the Lambert-Beer model. An in-vivo measurement is then performed (step 32) and based on the measurement at least one in-vivo based value is determined for the predetermined parameter. However, typically several wavelength-specific in-vivo based values are determined. The a priori relationship is then altered by adjusting the value of the tissue parameter so that it yields the best possible agreement between the in-vivo based values and the theoretical values of the predetermined parameter, i.e. the value of the tissue parameter is searched for, for which the in-vivo based values and the theoretical equivalent(s) correspond to each other. This value of the tissue parameter is regarded as the actual concentration of the blood substance.

The above theoretical a priori relationship is created in the manufacturing phase of the apparatus and stored in the memory of the apparatus. In connection with an in-vivo measurement, the apparatus may then determine, based on the relationship and in-vivo measurement signals, a set of wavelength-specific values for the predetermined parameter. The consistency of the wavelength-specific values is checked based on the a priori relationship and if consistency is not found directly, the a priori relationship is adjusted so that the set of wavelength-specific values indicate consistency. The value of the tissue parameter that yields the consistency determines the concentration.

Embodiments according to FIG. 3 are described in more detail in Applicant's U.S. patent application Ser. No. 11/780,525, filed Jul. 20, 2007. As is discussed therein, the predetermined parameter that is indicative of the wavelength-dependent effect of the in-vivo tissue on the measured signal and thus also on the consistency of the effect at different wavelengths may be, for example, the arterial oxygen saturation, $SpO_2$. The $SpO_2$ values obtained for different wavelength pairs are compared with each other and consistency is detected if these in-vivo based $SpO_2$ values are essentially the same. If this is not the case, the a priori relationship is adjusted to find out the value of tissue parameter for which the $SpO_2$ values are essentially the same.

The said predetermined parameter may also be an isobestic signal. In this embodiment for determining the hemoglobin concentration, the a priori relationship is thus formed between in-vivo and pseudo-isobestic signals. Consistency is achieved for the different wavelengths if a quotient of two pseudo-isobestic signals is essentially the same as its theoretical equivalent. The quotient, which is theoretically a constant parameter, is termed a pseudo-isobestic invariant (PII). The theoretical value of PII is determined and stored in the apparatus in the manufacturing phase of the apparatus. After this, when the apparatus is in use, the in-vivo measurements are made by measuring the transmission signals at three or more wavelengths and at least one in-vivo based value is determined for the PII based on the in-vivo measurement signals and the a priori relationship. The said at least one value is compared with the stored theoretical value of PII. If the obtained value(s) is/are substantially the same as the theoretical value, the effect of the tissue on the measurement signal can be regarded to be substantially consistent at the different wavelengths, and the a priori assumption (i.e. normal hemoglobin concentration) may be regarded as the correct one. However, typically there is a substantial difference between the theoretical value and the in-vivo based value(s). The a priori relationship is then altered to find out the hemoglobin concentration value for which the obtained PII value(s) correspond, as accurately as possible, to the theoretical value of the PII. The hemoglobin measure obtained in the above-manner is then supplied to the indicator unit 13.

A further alternative for determining the hemoglobin measure is to determine a parameter indicative of the blood volume of the subject. Since the hemoglobin concentration is inversely proportional to the blood volume, such parameter is also indicative of the hemoglobin concentration. One method for determining the blood volume of a subject is described in Applicant's U.S. patent application Ser. No. 12/163,305, filed Jun. 27, 2008. Thus, methods described in the said U.S. Patent Application may also be utilized to obtain the hemoglobin measure to be supplied to the indicator unit.

Above, the different embodiments of the hemoglobin measurement unit 11 of FIG. 1 were discussed. In the following, the embodiments of the physiological parameter unit 12 are discussed in more detail. As indicated above, the blood volume parameter(s) generated in unit 12 is/are indicative of changes in the volemia status of the subject, i.e., a parameter defined in unit 12 is responsive to changes in the blood volume of the subject. A plurality of blood volume parameters may be employed, which include parameters derived from heart rate, pulse rate, blood pressure, blood pulse pressure, and finger pletysmographic pulse amplitude, for example. The use of various specific parameters is discussed below.

In one embodiment, the physiological parameter unit may determine a pressure parameter that reflects cardiac left ventricular filling pressure, such as pulmonary artery occlusion pressure (PAOP) or, in other words, pulmonary artery wedge pressure (PWP), and supply the said parameter or a parameter derived from the said parameter to the indicator unit 13. The determination of PAOP may be carried out using a Swan-Ganz catheter together with pulmonary artery occlusion technique, for example. However, systolic blood pressure variation (SPV) and pulse pressure variation (PPV) can predict the response to fluid volume loading better and less invasively than PAOP.

In the embodiments determining SPV, the operation of unit 12 may be such that the peak values of the blood pressure in consecutive heart beats are detected first. Next, the maximum and minimum values of the peak (systolic) pressures are detected over one respiration cycle and the difference between the minimum and maximum values is calculated. In a mechanically ventilated patient, the difference is typically calculated in two segments: the delta down (dDown) and the delta up (dUp) that sum up to the total difference. Delta down is the systolic pressure change between the minimum minimum of the systolic pressure values and a reference systolic pressure, such as the average pressure measured during a short apnea period, while the delta up is the change between the maximum value and the said reference value. In normal volemia status (normovolemia), SPV is typically 8-10 mmHg, while the down and up components thereof, dDown and dUp, are typically 5-6 mmHg and 2-4 mmHg, respectively.

Higher SPV and dDown are good indicators of hypovolemia in a mechanically ventilated patient, in which dDown can be as much as 20 mmHg and is mainly responsible of the total pressure variation. Correspondingly, low values are indicative of hypervolemia.

Another possible blood volume parameter that may be determined in unit 12 is the delta arterial Pulse Pressure (dPP) that reflects pulse pressure variability over one respiration cycle. The value of dPP may be measured in percents, dPP=100*[PPmax−PPmin]/{[PPmax+PPmin]/2}, where PPmax is the maximum and PPmin the minimum of the pulse pressure values in one respiration cycle and each pulse pressure value represents the difference of the systolic and diastolic pressures in one heart beat. Low values of dPP are indicative of hypervolemia and high values of hypovolemia.

More information about the volemia status of a patient may be obtained by determining central venous pressure (CVP) or the pulmonary artery occlusion pressure after a rapid infusion of a certain amount of fluid, such as a 200 ml bolus. Thus, in this embodiment an infusion pump is needed to determine the blood volume parameter(s), cf. FIG. 7. Cardiac stroke volume (SV), cardiac output (CO), cardiac index (CI), or stroke index may also be estimated using transesophageal echocardiography ultra-sound or other appropriate techniques.

When an invasive monitoring of a patient is an issue, peripheral blood perfusion may be analyzed using (non-invasive) laser Doppler measurement or simply the $SpO_2$ measurement signal for obtaining information of the volemia status. The physiological parameter unit 12 now receives a plethysmographic pulse waveform measured from the subject and extracts respiration induced pulse variation by detecting the highest and the lowest plethysmographic pulse amplitude (PPA) over substantially one respiration cycle. The difference, the delta plethysmographic pulse amplitude dPPA in percentage from the average pulse height (dPPA=100*[PPAmax−PPAmin]/{[PPAmax+PPAmin]/2}), may indicate, similarly as dDown and SPV, the volemia status of a patient. Alternatively, the highest and lowest peak or valley values may be extracted, and the peak value and valley value variations may be calculated. A high variation of PPA or the systolic plethysmographic amplitude peak (PSA) over a respiration cycle, i.e. a large dPPA or dPSA, is a signature of hypovolemia. The plethysmographic waveform may be one of the waveforms used for the hemoglobin concentration measurement in the hemoglobin measurement unit 11, as is shown by the dashed lines in FIG. 1.

Figure 4:
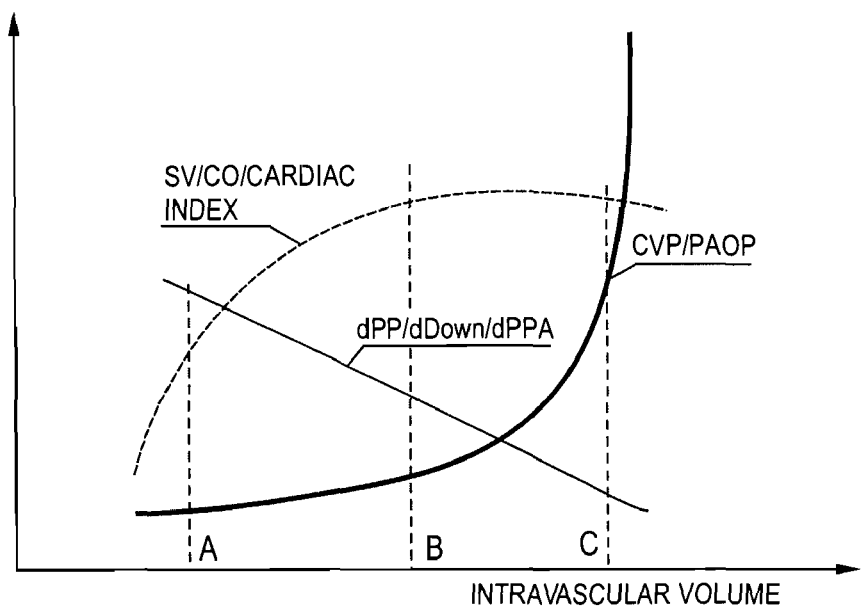
FIG. 4 illustrates the response of stroke volume and certain volemia parameters to an increase in intravascular volume.

FIG. 4 depicts typical behavior of the above blood volume parameters in response to a fluid expansion intervention at hypovolemia (around vertical line A), at normovolemia (around vertical line B), and at hypervolemia (around vertical line C). The thick continuous line illustrates the behavior of CVP and PAOP, the thin continuous line the behavior of dPP, dDown, and dPPA, and the dashed line the behavior of SV/CO/CT. Around vertical line A, CVP and PAOP may have no change or a small increase (small curve slope), and in case of severe hypovolemia even a small decrease. The stroke volume usually increases dramatically at hypovolemia. When more fluid is added into the patient plasma volume, the hemoglobin is diluted, but also the response to fluid expansion changes: CVP and PAOP around vertical line B typically show a clear increasing response, while the stroke volume does not increase any more. This indicates that further fluid expansions are not needed and the patient is adequately filled with fluids.

Still another physiological signal that the physiological parameter unit 12 may analyze is the electrocardiogram (ECG). Especially the respiratory sinus arrhythmia, RSA, the respiratory variation of the heart rate, or more accurately of the heart beat-to-beat interval, is indicative of the cardiac output (CO) variation over a respiration cycle. Again, a large variation may indicate an insufficient circulatory blood volume.

In certain cases the peripheral temperature and a peripheral temperature gradient along an extremity, such as an arm, or the core to peripheral (core to finger or core to toe) temperature difference may be indicative of the volume status of a patient. At hypovolemia the extremity temperature is low, because the low peripheral perfusion is insufficient to maintain a normal body temperature. When hypovolemia progresses, a temperature front (the region of high temperature gradient) may creep up the arm, which can be detected by multiple temperature sensors on the arm. The physiological measurement unit 12 may thus include a temperature measurement unit that includes several temperature channels, and the unit may calculate the temperature differences between the channels. An indication of a potential hypovolemia is obtained, if the temperature is lower than a certain threshold value or if the temperature difference exceeds a certain threshold limit.

Peripheral temperature and peripheral blood circulation correlate. Perfusion index, PI, or the plethysmographic pulse amplitude in a finger (measured through a pulse oximeter), is still an alternative physiological parameter that may indicate the volemia status of a patient.

Clinically the volemia status of a patient can also be estimated based on urine secretion or changes in venous blood oxygenation. In hypovolemia, urine secretion decreases as the blood flow to the kidneys decreases. Therefore, the physiological parameters that may be measured may be indicative of urine flow or volume of the bladder. The former parameter may be determined by a volume or mass flow measurement in a urine catheter or in a urine container. The bladder volume may be directly probed by ultra-sound imaging techniques without a urine catheter. The venous blood oxygenation reflects the metabolic activity of the patient. As the blood volume decreases, only the central organ blood circulation is maintained. As the brains consume a large portion of body oxygen, the central venous oxygenation tends to decrease in hypovolemia. The measurement of venous saturation, $SvO_2$, may be performed using a central venous catheter, but can be non-invasively estimated also based on expired oxygen gas concentration. Low expired oxygen percentage indicates low venous saturation. End tidal carbon dioxide, EtCO2, may also reflect the volemia status of a patient.

The above-described blood volume parameters that may be determined in the physiological parameter unit 12 are summarized in Table 1 below. The first four rows involve cardiovascular parameters, i.e., parameters that depend on the operation of the cardiovascular system and are thus rather closely related to blood volume changes, while while the last three rows show other parameters reflecting changes in blood volume. Table 2 shows the parameter values indicative of hypovolemia and hypervolemia. The threshold values shown in parenthesis are suggestive, and as is obvious, the value range between the thresholds of hypovolemia and hypervolemia is indicative of normovolemia.

TABLE 1

| | |
|---|---|
| Blood pressure and blood pressure variation | SPV, dDown, dPP, CVP, PAOP, PWP, systolic Blood Pressure (sysBP), Mean Arterial Pressure (MAP) |
| Heart rate variation | RSA |
| Cardiac ejection volume | CO, CI, SI |
| Blood circulation and peripheral perfusion, and respiratory blood circulation variation | PI, PPA, dPPA |
| Temperature | Finger/toe temperature, core-peripheral temperature gradient |
| Exhaled gas concentrations, venous oxygen saturation | SvO2, EtO2, EtCO2 |
| Urine secretion | Urine flow, bladder volume |

TABLE 2

| Physiological parameter | Parameter values indicative of hypovolemia | Parameter values indicative of hypervolemia |
|---|---|---|
| SPV | High values (>15 mmHg) | Low values (<9 mmHg) |
| Ddown | High values (>9 mmHg) | Low values (<5 mmHg) |
| DPP | High values (>13%) | Low values (<5%) |
| CVP | Low values (<4 mmHg) | High values (>15 mmHg) |
| PAOP | Low values (<3 mmHg) | High values (>10 mmHg) |
| SV/CO/Cardiac Index/Stroke Index | Positive response to fluid expansion | Non-responsive or negative response to fluid expansion |
| DPPA | High values (>9%) | Low values (<3%) |
| DPSA | High values (>5%) | Low values (<2%) |
| Temperature | Low values (<30° C.) | High values (>35° C.) |
| Core-finger temp gradient | High values (>5° C.) | |

The indicator unit 13 may use one or more of the above blood volume parameters for monitoring the fluid balance of a subject. In a simple embodiment, the indicator unit 13 may display the current values and the trends of both the hemoglobin measure and at least one parameter obtained from unit 12. In addition, the indicator unit may calculate a further blood volume parameter based on successive values of one blood volume parameter obtained from unit 12 and/or based on the concurrent values of several different blood volume parameters obtained from unit 12. Alternatively, such a further blood volume parameter may also be calculated in unit 12, i.e. the further processing of the basic blood volume parameters may be carried out in either unit or in both units.

The indicator unit may also calculate a quality/reliability index indicative of the quality/reliability of the measurement. The quality analysis methods employed may comprise a time correlation analysis of the hemoglobin measure and at least one blood volume parameter. The method may further comprise a Fourier analysis of the signals and spectral cross-correlation analysis of the spectra. A good correlation between the blood volume parameter(s) and the hemoglobin measure confirms the assessed volemia status of the patient. On the other hand, a poor correlation may indicate other causes for the abnormal parameter values.

The concurrent behaviour of the final blood volume parameter(s) and the hemoglobin measure indicates not only the volemia status but also the cause thereof, and thus also the form of fluid therapy needed. Based on the hemoglobin measure and the at least one final blood volume parameter, the indicator unit may therefore give an indication, such as a message, indicative of the cause of the volemia status and also of the correct form of fluid therapy. Table 3 below shows an example of the messages that may be displayed by the indicator unit. The different statuses shown in the cells of the table are provided with consecutive numbering shown in parenthesis. Cell (5) corresponds normal condition, while cells (1) and (9) represent typical cases where the hemoglobin measure confirms the cause of the volemia status. Cell (3) represents an unlikely case, whereas cell (7) represents a crisis situation.

TABLE 3

| Hemo-globin measure | Physiological parameter | | |
| --- | --- | --- | --- |
| | Indicative of hypovolemia | Indicative of normovolemia | Indicative of hypervolemia |
| High | HYPOVOLEMIA! Rapid blood plasma expansion with colloids. (1) | Confirm hemoglobin and normovolemia with other parameters. Consider increase of infusion. (2) | (3) |
| Normal | Hypovolemia due to possible major blood leakage. Check patient. (4) | Normal (5) | Stop fluid infusions. (6) |
| Low | Confirm hypovolemia with other parameters. Check patient oxygenation, consider blood transfusions. (7) | Check patient oxygenation, consider blood transfusions. (8) | HEMODILUTION! Stop fluid infusions, consider red blood cell transfusion. (9) |

If SPV and dDown are determined in the physiological parameter unit 12, the said parameters may be measured continuously and simultaneously with the hemoglobin concentration trend. Now better diagnosis of the volemia status of the patient is possible: if the hemoglobin concentration is increasing with the SPV and dDown, the indicator unit 13 may alert from hypovolemia caused by insufficient fluid infusion with a potential risk of sepsis and inflammatory state of a patient (cell (1) of Table 2). If the hemoglobin trend is not increasing, but SPV and dDown are high, the unit may suggest that a patient is losing blood, the plasma and blood cells, to body cavities (cell (4) of Table 2). In a similar manner, hypervolemia is expected, if the hemoglobin concentration trend is in down slope and the SPV and dDown are small or at normal level (cells (8) and (9) of Table 2).

In one embodiment, the indicator unit may thus display the SPV, dPP and/or dDown and the hemoglobin concentration trends and indicate in an alarm or message field additional information about the possible reasons of the volemia status. Although a clinician may directly deduce the correct form of fluid therapy based on the reasons indicated by the indicator unit, the alarm or message field may contain, in addition to the reasons, the suggested fluid therapy form.

In the embodiments employing dPPA, the operation of the indicator unit 13 may also be based on certain threshold values. A plethysmographic pulse variation larger than about 9-10% may identify patients that can benefit from fluid expansion. The sensitivity and specificity of this method to classify the patients as responders and non-responders to fluid expansion is as good as for dDown and SPV. The non-invasivity of the plethysmographic method is a substantial advantage, because it is always available when the oxygen saturation $SpO_2$ is measured, i.e. in all acute and most of the non-acute care areas.

Although the blood volume parameter(s) may be determined continuously, it is also possible that a sufficient change, such as about 10%, in the hemoglobin measure triggers a more detailed analysis in the physiological parameter unit 12.

Figure 5:
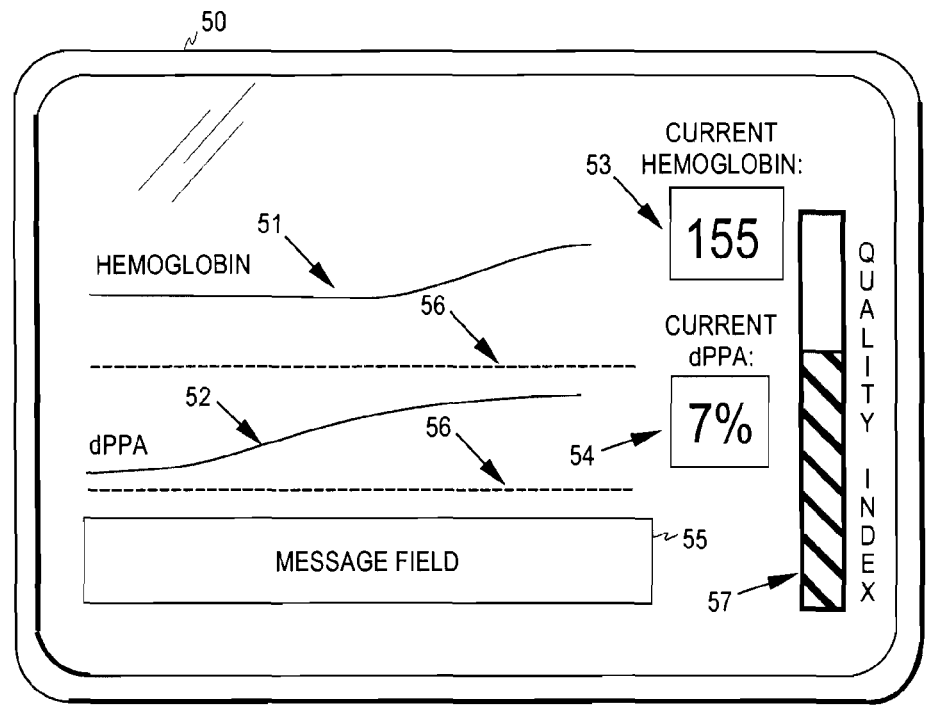
FIG. 5 shows an example of the information displayed to the user of the system.

In one embodiment, the indicator unit 13 thus displays the trend of the hemoglobin concentration together with that of at least one blood volume parameter obtained from the physiological parameter unit. FIG. 5 shows a display 50 of the indicator unit 13, with an example of the information content displayed to the user. In this example, the indicator unit displays both the trend of the hemoglobin concentration measured by the hemoglobin measurement unit and the trend of dPPA measured by the physiological parameter unit. The corresponding curves are denoted with reference numbers 51 and 52. The current values of the said variables may also be displayed, as is shown in boxes 53 and 54. The screen of the display may also include a message field 55 for displaying the messages shown in table 2. A typical value range of the blood volume parameter may be incorporated in the parameter display trend, as is denoted with dashed lines 56. Based on the quality/reliability index, the indicator unit may also display a quality indicator indicative of the quality of the measurement. In this example, the quality indicator is in the form of a bar 57, whose height depends on the value of the quality index.

Figure 6:
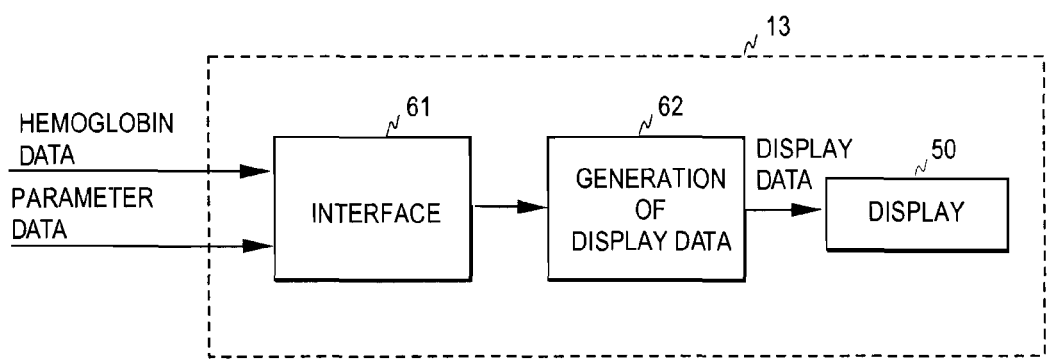
FIG. 6 illustrates an example of the indicator unit.

Although, units 11 to 13 may be integrated into one compact measurement device, the indicator unit may also be a separate device. As is shown in FIG. 6, the indicator unit 13 may in this case comprise an interface unit 61 configured to receive the hemoglobin measure and blood volume parameter(s) from one or more external measurement devices. In this way, existing measurement devices may be used to supply the hemoglobin measure and one or more blood volume parameters to the indicator unit that indicates the concurrent behavior of hemoglobin and at least one blood volume parameter. The received data is supplied to a display control unit 62 that controls a display 50, which may be an integral part of the indicator unit or a separate unit. The amount of data processing to be carried out in unit 62 based on the received hemoglobin and parameter data depends on the information to be displayed. As discussed below, especially the indication of various quality indices and/or indicators requires data processing.

An example of the operation of the indicator unit 13 will now be described in more detail with reference to an embodiment of the system in which a hemoglobin measure is calculated in the hemoglobin measurement unit 11 and dPPA and dPP are calculated in the physiological parameter unit 12. The respiratory variation in the plethysmographic pulse amplitude, dPPA, and in the arterial pulse pressure, dPP, are presented in percentages with a threshold value of 9% and 13% for hypovolemia, respectively. The hemoglobin measure indicates the hemoglobin concentration in g/L. Three possible analysis methods will be discussed: linear regression with parameter correlations, logistic regression with hypovolemia and hypervolemia indicators, and a Bayesian probability estimation for hypovolemia.

The patient blood plasma volume V(t) may be derived from the hemoglobin concentration THb(t) through the following equation: $V(t)/V0=THb0/THb(t)$, in which V0 and THb0 are the blood plasma volume and hemoglobin concentrations, respectively, at baseline time. The said parameter values may be determined from a blood sample before a surgery, for example. The blood volume is thus inversely proportional to the hemoglobin concentration. This is a consequence of the fact that in the absence of blood leaks, the hemoglobin is confined in blood plasma only. The blood volume estimate calculated according to the above equation based on the hemoglobin measure THb(t) is termed hemoglobin volume estimate in this context.

An estimate for the blood plasma volume may also be derived from the blood volume parameters dPP and dPPA. This estimate is here termed the physiological volume estimate. The calculation of the physiological volume estimate may be based on an a priori linear regression model created during extensive clinical testing, in which the volume V and the blood volume parameters, dPP and dPPA, have been related. The linear regression model may be written as follows: $V(t)=b0+b1 \times dPP+b2 \times dPPA+ePhys$, where b0, b1, and b2 are regression coefficients and ePhys is a residual error parameter that has a zero mean. The regression coefficients may be determined for any number of physiological parameters that are indicative of a patient volemia response. In a simple embodiment only one physiological parameter, for instance dPPA, may be utilized. The regression model may also be created for the combination of the physiological parameters and the hemoglobin measure. In this case the a priori regression model is as follows: $V(t)=a0+a1 \times V0 \times THb0/THb(t)+a2 \times dPPA+a3 \times dPP+E$, in which the coefficients a0, a1, a2, and a3 are determined in clinical tests, and E is the residual error term.

In the above first example, two blood volume parameters are used to obtain the physiological volume estimate and the continuous hemoglobin measurement carried out in unit 11 is utilized to obtain the hemoglobin volume estimate. The indicator unit 13 may analyze the two blood volume estimates by several standard means. The time evolution of the volume estimates may be presented as one or two separate plots. The length of the data presented may be user selectable, but is preferably 30 to 60 minutes. For analyzing the time trend over a predetermined time interval, for instance over the last 30 minutes, the volume estimates may be correlated with time. Positive correlations indicate increasing volume estimates. If the time evolution is not displayed explicitly to the observer, a four field time evolution measure and the current physiological and hemoglobin volume estimates may be displayed, for example. The four field time evolution measure may show the time correlation coefficients, RtHb and RtPhys, in a x-y plot where the axes divide the area confined by points (1,1), (1,−1), (−1,−1), and (−1,1) into four fields that locate around the origo. The display may also be simplified to a simple gradient or sign display, in which the "+" sign indicates a positive time trend and the "−" sign a negative one. The two volume estimates agree when both are of the same sign. Opposite signs indicate a controversial situation, which should be analyzed with more physiological information and observing the patient. The time correlation coefficients comprise an example of the quality index, while the four field x-y plot with the information derived from time correlation coefficients is an example of the quality indicator.

The indicator unit 13 may also use regression and/or correlation analyses to determine how well the physiological volume estimate explains the variations in the hemoglobin volume estimate, or vice versa. A simple method is to show the two volume estimates in a x-y plot as pairs $Xi=V_{Phys}$ and $Yi=V_{Hb}$, in which the hemoglobin volume estimate $V_{Hb}$ is on the y-axis and the physiological volume estimate $V_{Phys}$ is the independent variable x. The index i of the paired data may, for example, cover a time interval of the last 30 minutes. The regression model thus is: $V_{Hb}=b0+b1 \times V_{Phys}+e$, in which e is the error term. A quality/reliability index may now be either or both of the variances Sx or Sy, or the covariance $Sxy=1/(n-1) \times sum\{(Xi-<X>)(Yi-<Y>)\}$, where <X> and <Y> are the means of the x- and y-data, respectively. A sign analysis of the covariance may provide similar information as the above-mentioned four field indicator. Alternative quality indices that may be used are correlation coefficient Rxy=Sxy/Sx/Sy, i.e., Pearson's correlation coefficient, or residual variance $E^2=sum(e^2)$. In the above model of one independent variable, the explanation degree $R^2=(Rxy)^2$; $R^2=1$ implies a perfect explanation, while $R^2=0$ implies that the x and y variables are fully independent. independent. $R^2$ and Rxy are thus other examples of the quality/reliability index.

When the combined regression model with the physiological and hemoglobin volume estimates is used, the time correlations may be analyzed similarly as discussed above. The covariance between each parameter pair of the model may also be calculated. A matrix of the covariances may be used to select a regression model that minimizes the total residual error. For instance, if the covariance matrix indicates that one of the parameters does not contribute positively to the total degree of explanation of the model, the parameter may be left out and the remaining blood volume model may be used as an estimate of the patient volume status. Such a covariance matrix may also serve as the quality indicator of the measurement.

As mentioned above, the indicator unit 13 may also perform a logistic regression analysis. This analysis is appropriate when the dependent variable, i.e., the one that is explained, is a binary variable, such as an event that may be true or false. The logistic regression is thus appropriate, if the probability of hypovolemia or hypervolemia of a patient is to be analyzed. For the probability estimation a logistic function p(z) is typically used, the said function being of the form $p(z)=1/(1+e^{-z})$, where z is a regression expression. The regression expression for the event of hypovolemia may be a linear combination of the blood volume parameters and the hemoglobin volume estimate: $z=c0+c1 \times V0 \times THb0/THb(t)+c2 \times dPPA+c3 \times dPP$, for instance. The coefficients c0-c3 may be determined similarly as in case of linear regression. The optimal values of the coefficients depend on the sensitivity and the specificity that is required for the hypovolemia detection. For instance, if all hypovolemia cases are to be detected at the expense of the number of false hypovolemia detections, high sensitivity is preferred. If all detected cases must really be hypovolemia events, high specificity is to be required. The sensitivity and specificity of the hypovolemia or hypervolemia detection depend also on the threshold set for the probability function, the crossing of which threshold is indicative of hypovolemia or hypervolemia. The further the actual 'measured' probability is from the threshold value, the more reliable is the detection. The distance from the threshold value may also serve as the quality/reliability index.

In the above two examples, data regression was used to obtain a reliable volume estimate and/or the probability of a certain volume status in a patient. In a Bayesian formulation, the probability of a certain volume status of a patient is obtained without regression by using extensive training data to obtain the probabilities of certain parameter combinations in the predetermined volume status of a patient. For instance, the Bayesian formula for the hypovolemia event may be written as follows:

$$P(hypovolemia|observed[THb,dPPA,dPP]) = P(observed[THb,dPPA,dPP]|hypovolemia) \times P(hypovolemia)/P(observed[THb,dPPA,dPP]),$$

where P(hypovolemia|observed[THb,dPPA,dPP]) is the probability of hypovolemia with the parameter combination [THb,dPPA,dPP] measured from the patient; P(observed [THb, dPPA, dPP]|hypovolemia) is the probability of the parameter combination in the training data, when the patient is hypovolemic; P(hypovolemia) is the probability of the hypovolemic state in the whole training data; and P(observed [THb, dPPA, dPP]) is the probability of the particular parameter combination in the whole training data. The Bayesian approach thus allows to describe the behaviour of patient data based on how the same data has behaved in the past in a similar clinical setting, i.e. in a training setting. Another example of the quality indicator could be a bar indicator like the one shown in FIG. 5, which is now provided with a certain threshold value marked on the bar. Hypovolemia detection can then be confirmed, when the bar indicates sufficiently higher Bayesian probability values than the predetermined threshold level.

Figure 7:
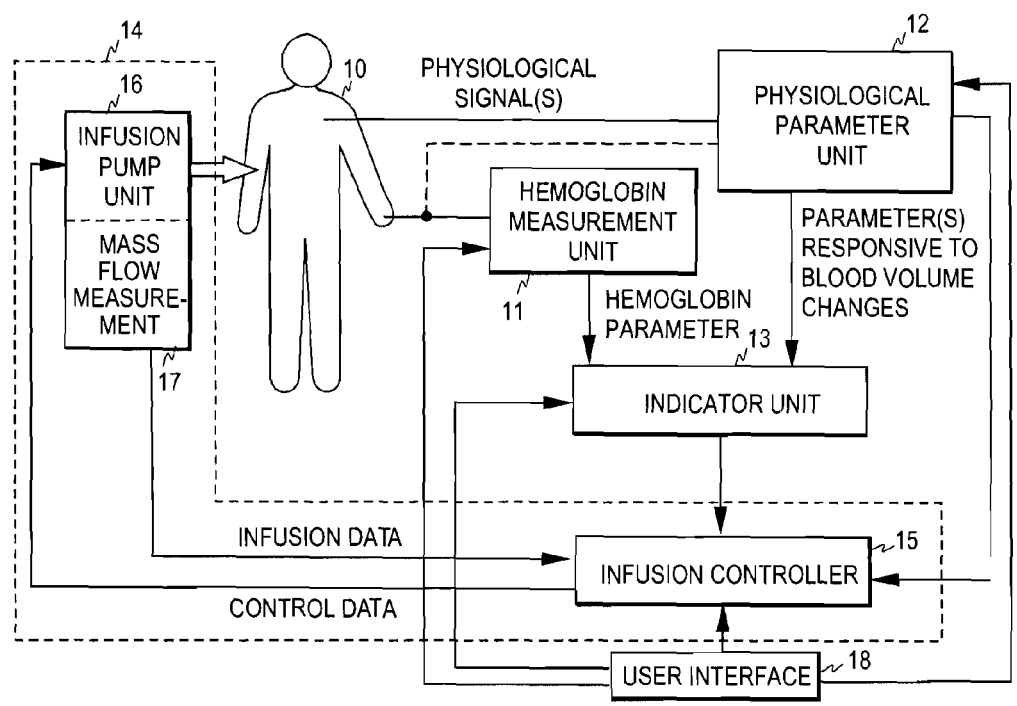
FIG. 7 illustrates one embodiment of an automated infusion system based on the monitoring system of FIG. 1.

FIG. 7 illustrates a further embodiment of the system for monitoring the fluid balance of a subject. In this example, the system according to FIG. 1 is augmented by an infusion control system 14 comprising an infusion controller 15 and an infusion pump unit 16 that includes the infusion pumps needed for the different infusion fluids to be infused into the subject. The infusion pump unit is further provided with a mass flow measurement unit 17 for measuring the amount or rate of each fluid infused into the subject. The automation degree of the infusion control system may vary. However, in all embodiments the user may override the automated control to assume manual control of the infusion through a user interface 18.

As discussed above, the infusion control system may also be used for automatically repeated fluid expansions, after which the CVP, PAOP, SV, or CO responses are observed. The fluid expansion may be repeated until a desired response in these parameters is obtained. The physiological parameter unit 12 may give the infusion controller 15 a command to administer a bolus needed to measure the response.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for monitoring fluid balance status of a subject, the method comprising:
   non-invasively determining in-vivo a hemoglobin measure indicative of hemoglobin concentration in blood of a subject, wherein the determining includes determining successive values of the hemoglobin measure;
   defining at least one physiological parameter responsive to blood volume changes in the subject, wherein the defining includes defining successive values for the at least one physiological parameter; and
   indicating concurrent behavior of the hemoglobin measure and the at least one physiological parameter, thereby to give an indication of fluid balance status of the subject.

2. The method according to claim 1, wherein the defining the at least one physiological parameter includes defining a cardiovascular parameter.

3. The method according to claim 1, wherein the indicating includes displaying prevailing trends of the hemoglobin measure and the at least one physiological parameter graphically.

4. The method according to claim 1, wherein the indicating includes
   selecting, based on the concurrent behavior, a message indicative of the fluid balance status of the subject; and
   displaying the message to a user.

5. The method according to claim 4, wherein the indicating includes selecting the message, in which the message indicates at least one of a cause of the fluid balance status and a suggestion of a fluid therapy form.

6. The method according to claim 4, wherein the selecting includes selecting the message based on current values of the at least one physiological parameter and the hemoglobin measure.

7. The method according to claim 1, wherein
   the non-invasively determining the hemoglobin measure includes acquiring measurement signals from the subject substantially continuously through a multi-wavelength pulse oximeter; and
   the at least one physiological parameter is defined from the measurement signals.

8. The method according to claim 1, wherein the indicating includes a administering a fluid bolus to the subject.

9. The method according to claim 4, further comprising determining a quality index indicative of reliability of the fluid balance status indication.

10. The method according to claim 1, further comprising determining a quantitative estimate of blood volume of the subject.

11. An in-vivo method for monitoring fluid balance of a subject, the method comprising:
    non-invasively determining a hemoglobin measure in a hemoglobin measurement unit that is indicative of hemoglobin concentration in blood of a subject, wherein the determining includes determining successive values of the hemoglobin measure;
    defining at least one cardiovascular parameter in a physiological parameter unit that is responsive to blood volume changes in the subject, wherein the defining includes defining successive values for the cardiovascular parameter; and
    indicating concurrent behavior of the hemoglobin measure and the cardiovascular parameter with an indicator unit to give an indication of fluid balance status of the subject.

12. The method according to claim 11, wherein the indicating includes displaying prevailing trends of the hemoglobin measure and the cardiovascular parameter graphically.

13. The method according to claim 11, wherein the indicating includes
  selecting, based on the concurrent behavior, a message indicative of the fluid balance status of the subject; and
  displaying the message to a user.

14. The method according to claim 13, wherein the indicating includes selecting the message, in which the message indicates at least one of a cause of the fluid balance status and a suggestion of a fluid therapy form.

15. The method according to claim 11, wherein
  the non-invasively determining the hemoglobin measure includes acquiring measurement signals from the subject substantially continuously through a multi-wavelength pulse oximeter; and
  the defining includes deriving the at least one physiological parameter from the measurement signals.

16. The method according to claim 11, wherein the indicating includes a administering a fluid bolus to the subject.

17. The method according to claim 13, further comprising determining a quality index indicative of reliability of the fluid balance indication.

18. The method according to claim 11, further comprising determining a quantitative estimate of blood volume of the subject.

19. The method according to claim 1, wherein the at least one physiological parameter includes a pulse pressure variation and/or a blood pressure variation.

20. The method according to claim 11, wherein the physiological parameter unit further defines a respiratory variation for the cardiovascular parameter.

* * * * *